United States Patent [19]
Grossman

[11] Patent Number: 6,001,570
[45] Date of Patent: *Dec. 14, 1999

[54] COMPOSITIONS, METHODS, KITS AND APPARATUS FOR DETERMINING THE PRESENCE OR ABSENCE OF TARGET MOLECULES

[75] Inventor: Abraham Grossman, Pleasantville, N.Y.

[73] Assignee: InVitro Diagnostics, Inc.

[ * ] Notice: This patent issued on a continued prosecution application filed under 37 CFR 1.53(d), and is subject to the twenty year patent term provisions of 35 U.S.C. 154(a)(2).

[21] Appl. No.: 08/801,154

[22] Filed: Feb. 18, 1997

[51] Int. Cl.⁶ ..................................... C12Q 1/68
[52] U.S. Cl. ............... 435/6; 435/91.2; 536/24.3
[58] Field of Search ........... 435/6, 91.2, 91.21, 435/91.31; 536/24.3

[56] References Cited

U.S. PATENT DOCUMENTS

| | | | |
|---|---|---|---|
| 4,786,600 | 11/1988 | Kramer | 435/235 |
| 4,883,750 | 11/1989 | Whiteley | 435/6 |
| 5,112,734 | 5/1992 | Kramer | 435/6 |
| 5,312,527 | 5/1994 | Mikkelsen | 204/153.12 |
| 5,407,798 | 4/1995 | Martinelli | 435/6 |
| 5,496,938 | 3/1996 | Gold et al. | 536/22.1 |
| 5,503,978 | 4/1996 | Schneider | 435/6 |
| 5,567,588 | 10/1996 | Gold | 435/6 |
| 5,582,981 | 12/1996 | Toole et al. | 435/6 |
| 5,591,578 | 1/1997 | Meade | 435/6 |
| 5,616,478 | 1/1997 | Cheiverin | 435/91.2 |
| 5,652,107 | 7/1997 | Lizardi | 435/6 |

OTHER PUBLICATIONS

Helena V. Chetverina and Alexander B. Chetverin Cloning of RNA molecules in vitro, Nucleic Acids Research 1993, vol. 21, No.10.

Vladmir D. Axelrod, Eileen Brown, Christine Priano and Donald R. Mills Coliphage Q RNA Replication: RNA Catalytic for Single–Strand Release Microbiology 184, 595–608 (1991).

Larry Gold, Barry Polisky, Olke Uhlenbeck, Michael Yarus Diversity of Oligonucleotide Functions, Annu. Rev. Biochem 1995. 64:763–97.

Stefanie J. Klug & Michael Famulck , All you wanted to know about Selex Molecular Biology Reports 20:97–107, 1994.

David Brown and Larry Gold, Selection and Characterization of RNAs Replicated Q Replicase, Biochemistry 1995, 34, 14775–14782.

David Brown and Larry Gold, Template Recognition by an RNA–Dependent RNA Polymerase: Identification and Characterization of Two RNA Binding Sites on Q Replicase, Biochemistry 1995, 34, 14765— 14774.

*Primary Examiner*—Scott W. Houtteman
*Attorney, Agent, or Firm*—Anthony J. Janiuk

[57] ABSTRACT

The present invention is directed to methods, compositions, kits and apparatus; to identify and detect the presence or absence of target analytes. The embodiments of the present invention have utility in medical diagnosis and analysis of various chemical compounds in specimens and samples, as well as the design of test kits and apparatus for implementing such methods.

10 Claims, 1 Drawing Sheet

SEQUENCE LISTING

```
<160> NUMBER OF SEQ ID NOS: 18

<210> SEQ ID NO 1
<211> LENGTH: 50
<212> TYPE: DNA
<213> ORGANISM: adeno-associated virus 2

<400> SEQUENCE: 1
cgcgttcgtc ctcactctct tccgcatcgc tgtctgcgag ggccagggcc           50

<210> SEQ ID NO 2
<211> LENGTH: 37
<212> TYPE: DNA
<213> ORGANISM: adeno-associated virus 2

<400> SEQUENCE: 2
tcgaggccct ggccctcgca gacagcgatg agctccc                         37

<210> SEQ ID NO 3
<211> LENGTH: 33
<212> TYPE: DNA
<213> ORGANISM: adeno-associated virus 2
```

-continued

<400> SEQUENCE: 3
gggagctcat cgctgtctgc gagggccagg gcc                          33

<210> SEQ ID NO 4
<211> LENGTH: 22
<212> TYPE: DNA
<213> ORGANISM: adeno-associated virus 2

<400> SEQUENCE: 4
aagagagtga ggacgaacgc gc                                      22

<210> SEQ ID NO 5
<211> LENGTH: 26
<212> TYPE: DNA
<213> ORGANISM: adeno-associated virus 2

<400> SEQUENCE: 5
tcgagcgcgt tcgtcctcac tctctt                                  26

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: ARTIFICIAL
      PROBE SEQUENCE

<400> SEQUENCE: 6
gggaagagag ugaggacgaa cgcgc                                   25

<210> SEQ ID NO 7
<211> LENGTH: 30
<212> TYPE: RNA
<213> ORGANISM: Artificial Sequence
<220> FEATURE:
<223> OTHER INFORMATION: Description of Artificial Sequence: ARTIFICIAL
      PROBE SEQUENCE

<400> SEQUENCE: 7
ggcccuggcc cucgcagaca gcgaugagcu                              30

<210> SEQ ID NO 8
<211> LENGTH: 54
<212> TYPE: RNA
<213> ORGANISM: Artificial Sequence
<220> FEATURE:
<223> OTHER INFORMATION: Description of Artificial Sequence: ARTIFICIAL
      PROBE SEQUENCE

<400> SEQUENCE: 8
ggcccuggcc cucgcagaca gcgaugagcu gggaagagag ugaggacgaa cgcg   54

<210> SEQ ID NO 9
<211> LENGTH: 35
<212> TYPE: RNA
<213> ORGANISM: Artificial Sequence
<220> FEATURE:
<223> OTHER INFORMATION: Description of Artificial Sequence: ARTIFICIAL
      PROBE SEQUENCE

<400> SEQUENCE: 9
ggugggcgca gcgucaauga cgcugacggu acacc                        35

<210> SEQ ID NO 10
<211> LENGTH: 39

```
<212> TYPE: DNA
<213> ORGANISM: Artificial Sequence
<220> FEATURE:
<223> OTHER INFORMATION: Description of Artificial Sequence:  cDNA for
      aptamer

<400> SEQUENCE: 10
tcgaggtggg cgcagcgtca atgacgctga cggtacacc                         39

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: cDNA for
      aptamer

<400> SEQUENCE: 11
tcgaggtgta ccgtcagcgt cattgacgct gcgcccacc                         39

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:  cDNA for
      aptamer

<400> SEQUENCE: 12
tcgaggtggg cgcagcgtca aagct                                        25

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: cDNA for
      aptamer

<400> SEQUENCE: 13
agctttgacg ctgcgcccac c                                            21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:  cDNA for
      aptamer

<400> SEQUENCE: 14
aatgacgctg acggtacacc                                              20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: cDNA for
      aptamer

<400> SEQUENCE: 15
tcgaggtgta ccgtcagcgt catt                                         24

<210> SEQ ID NO 16
<211> LENGTH: 21
<212> TYPE: RNA
<213> ORGANISM: Artificial Sequence
```

-continued

```
<220> FEATURE:
<223> OTHER INFORMATION: Description of Artificial Sequence:  Aptamer
                        RNA

<400> SEQUENCE: 16 gguggggcgca gcgucaaagc u                                                    21

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence:  Aptamer
                        RNA

<400> SEQUENCE: 17
gggaaugacg cugacgguac acc                                                   23

<210> SEQ ID NO 18
<211> LENGTH: 44
<212> TYPE: RNA
<213> ORGANISM: Artificial Sequence
<220> FEATURE:
<223> OTHER INFORMATION: Description of Artificial Sequence:  Aptamer
                        RNA

<400> SEQUENCE: 18 gguggggcgca gcgucaaagc ugggaaugac gcugacggua cacc                           44
```

COMPOSITIONS, METHODS, KITS AND APPARATUS FOR DETERMINING THE PRESENCE OR ABSENCE OF TARGET MOLECULES

FIELD OF THE INVENTION

The present invention is directed to methods, compositions, kits and apparatus to identify and detect the presence or absence of target analytes. The embodiments of the present invention have utility in medical diagnosis and analysis of various chemical compounds in specimens and samples, as well as the design of test kits and apparatus for implementing such methods.

BACKGROUND OF THE INVENTION

Molecular biology advances in the last decade gave great promise for the introduction of new, sensitive technologies to identify various analytes in test specimens, including the ability to diagnose cancer, infectious agents and inherited diseases. Clinical molecular diagnostics depend almost exclusively on restriction enzyme analyses and nucleic acid hybridization (Southern and Northern blots) (Meselson and Yuan, 1968, Southern, 1975). Clinical tests based on molecular biology technology are more specific than conventional immunoassay procedures and can discriminate between genetic determinants of two closely related organisms. With their high specificity, nucleic acid procedures are very important tools of molecular pathology. However, nucleic acid procedures have limitations, the most important of which are the procedures consume time, they are labor intensive, and have low sensitivity (Nakamura 1993).

The subsequent attachment of radioactive or fluorescent reporting molecules to probes increased the sensitivity of nucleic acid technology. A signal from a single hybridization event could be amplified several hundred fold. The nature of the signal allowed simple visualization of each probe-target complex. However, nucleic acid reaction kinetics dictate that only 1–5% of the target molecules in a molecular pool of specimen are available for hybridization. Thus, there must be at least $5-10\times10^6$ cells (or 5–10 ug of purified nucleic acid) in a specimen in order to identify affected cells with one target nucleic acid molecule in each specimen.

Another approach used to increase test sensitivity is to amplify target molecules. This was achieved by direct PCR and other target amplification methods (Saiki et al, 1985, Mullis et al., 1986). However, the use of PCR technology has been limited mainly to research applications and to use in a few sophisticated clinical reference laboratories. The power and sensitivity of PCR creates its major limitation—non-specific and false-positive amplification.

False amplification of sequence-markers for mutant oncogenes, chromosomal rearrangements or viral infectious pathogens in a clinical specimen may have profound implications for patients undergoing therapy as a result of the test results. It is technically difficult to distinguish a truly positive PCR product from the products created by non-specific amplification or by contamination with exogenous or previously-amplified DNA. There are several approaches to reducing the occurrence of false positive signals. (Saiki, 1990, Rys and Persing, 1993), however, these approaches have not brought PCR methods to the clinical laboratory.

False negative results represent another limitation of PCR-based methods. False negative results may occur due to possible inhibitory effects of the specimen on the reaction, nonoptimal concentrations of the components, or enzymes in a reaction mixture (Qi An et al., 1995). False negative results have serious implications for individuals, who in reliance on the test results do not receive timely therapy.

Amplification systems based on an enzyme of the Q-beta bacteriophage have been proposed. The Q-beta bacteriophage contains a plus-strand RNA. The plus-strand RNA serves as both mRNA for viral protein synthesis and a template for an RNA-dependent RNA polymerase, Q-beta replicase. In the presence of the plus-strand RNA, and other cofactors, the enzyme Q-beta replicase synthesizes the complementary minus-strand RNA. The minus-strand, in a turn, can serve as a template for plus-strand RNA synthesis. There is potential to amplify RNA molecules exponentially in the interaction between Q-beta replicase and its two templates—the plus and minus RNA molecules (Weissmann et al., 1968, Dobkin et al., 1979).

A number of strategies have been devised to use Q-beta native RNA templates to propagate heterologous RNA inserts (Fernandez A., 1991, Munishkin et al., 1991, Wu et al., 1992). Recombinants that form more-stable two- and three-dimensional intramolecular structures have decreased tendency to form extended plus-minus RNA—RNA duplexes during replication, which results in increased synthesis of new RNA strands (Priano et al., 1987).

Chimeric Q-beta RNA template molecules with inserts containing heterologous sequences combine two functions that make them unique among other nucleic acid molecules and position them into a special group—they can serve simultaneously as both probes and reporting molecules. As a nucleic acid fragment with a specific nucleotide sequence, the insert retains its conventional hybridization ability with high specificity to its complementary target molecules, while the whole molecule maintains its tremendous efficacy for replication. Only a few target molecules are required for detection to be amplified a hundred billion times. Theoretically, a single DNA target molecule can be detected by Q-beta replicase, which can use a single MDV-I chimeric molecule as a template to produce a detectable signal after less than one hour (Lizardi et al., 1988, Pritchard and Stefano, 1990).

Being very sensitive by nature, the methods based in Q-beta replicase technology are subject to various sources of potential contamination. The major problem of "false positives" in Q-beta replicase experiments is from the template molecules, which do not hybridize to the target nucleic acid but are still present in the reaction as contaminant-templates for Q-beta replicase.

One strategy to eliminate background created by probes that do not hybridize to the target and has been described independently in two publications (Martinelli et al., 1995, Tyagi et al., 1996). Martinelli and Tyagi propose that a chimeric template, MDV-I RNA with inserted probe sequences, be divided into halves. Each half is composed of sequences homologous to the target molecule (probes) and half of the template molecule. Neither of these halves can be amplified separately because neither of them contains the full template complement necessary for replication. The probes are designed in such a way that upon hybridization to the target molecule, they are positioned adjacent to each other, binding to the target. The terminal nucleotides of these 'binary probes' are ligated by DNA ligase and the restored template-reporter can be amplified by Q-beta replicase. This strategy was applied to MDV-I DNA (Martinelli et al., 1995) and later with MDV-I RNA as a template (Tyagi et al., 1996).

One of the major advantages that differentiates Q-beta amplification assays from PCR is that Q-beta can amplify a single reported MDV-I molecule up to a hundred billion fold isothermally in less than one hour. An easily manageable, extremely sensitive and highly specific diagnostic method, Q-beta replicase assays have the same flaws common to all other methods of targeting nucleic acid molecules. None of them can be applied to proteins.

In any sample, the number of protein molecules of one kind is usually several times higher than the corresponding mRNA, and several hundred times higher than the number of genes encoding them. Using antigen-specific antibodies is a routine procedure in the modern diagnostic industry, although antibody development and purification usually require laborious work. The specificity of tests based on monoclonal antibodies depends on the capacity of antibodies to differentiate between antigens, and might approach the specificity of tests based on nucleic acid hybridization. The sensitivity of these tests, however, is routinely significantly lower than tests based on nucleic acid hybridization, even though the number of protein target molecules in each cell is relatively higher than the nucleic acid molecules corresponding to them. It is desirable to use proteins as the targets in diagnostic tests because of their abundance.

Thus, a need exists for improved diagnostic and analytical methods to detect the presence or absence of target molecules. A need also exists to detect non-nucleic acid analytes with nucleic acid chemistry.

A new technology, SELEX (Systematic Evolution of Ligands by EXponential enrichment) (Tuerk and Gold, 1990) is a powerful tool to identify nucleic acid ligands with the ability to bind to compounds of various chemical compositions, including important medicinal targets. Similar to monoclonal antibodies, these ligands, resulting from 'in vitro selection' demonstrate high affinity and specificity with various compounds, including proteins (Ellington and Szostak, 1990).

The starting point for the SELEX process is a pool of nucleic acid molecules with defined sequences into which another oligonucleotide from a library of randomized sequences is embedded. The SELEX procedure involves several cycles, each of which comprises affinity selection of the oligonucleotide from a heterogeneous population of nucleic acids (RNA or DNA) by target analyte, partition of the annealed nucleic acid and target, and amplification of the high affinity oligonucleotide subset. Each species of randomized nucleotides in the original library demonstrates a different degree of proclivity to the target molecule as a result of their sequence-dependent tertiary structure. The confiormational variability among members of such a library make it possible for the target molecule to select the RNA (or DNA) ligand with the highest affinity, termed aptamer (from Lat. 'aptus'—to fit ), even though the fraction of functional molecules in the original library is very small. Positive selection through a number of cycles will progress toward the molecule with highest affinity to the target analyte and will reduce background. The number of cycles used depends upon the frequency of the 'winner' aptamer in the pool of oligonucleotides at the end of each cycle, and varies from 3 to 24 with an average 10–12, depending on the nature of the target and composition of the original library (Gold et al., 1995). Twenty-five fully randomized four nucleotides ($4^{25}=10^{15}$ species) is the practical limit of saturation in a SELEX process. The original complexity of the pool of randomized nucleotides generated is ample, considering that the number of antibodies produced by mice is five orders lower (Klug and Famulok, 1994).

As a result of 'in vitro selection', as few as three winners and as many as fourteen 'aptamer-winners' are SELEXed at the end of the experiments for different targets (Gold et al., 1995). High affinity oligonucleotides have already been identified for more than forty different compounds. In general, aptamers from in vitro selection resemble protein antibodies to a great extent; they are highly specific for various antigens and more than one 'winner' specific for different epitopes can be generated for the same target molecule. Their affinities reach the $K_d$ level as low as 1.0 nM (Schneider et al., 1995) or even nanomolar fractions (Bock et al., 1992, Kubik et al., 1994), which make them as good as or even better than proteinous antibodies. The aptamers make contact with the target through the domain of 10–15 nucleotides in the region of the 300–400 $A^2$, which is approximately equal to the antigen recognition region of the Fab fragment of antibodies (Gold et al., 1995). Analogously, nucleic acid ligands with high affinity to the target analytes are termed "nucleic acid antibodies'. Similar to protein antibodies, nucleic acid antibodies can be modified in a such a way as to become carriers of a drug or other small molecule to the targets, making them a new, useful tool in therapeutic medicine, and they can be protected from endonucleases when they are used for therapeutic purposes or in diagnostic procedures on easy-to-obtain human blood or urine specimens (Pieken et al., 1991).

One of SELEX's major limitations, besides being technically very laborious and time consuming, follows from the conformational complexity of winning aptamers which determines their high affinity to the target analyte. The complex tertiary structure of the aptamers may affect the outcome of amplification performed by PCR or during cDNA synthesis using reverse transcriptase enzyme as the component of each cycle. Molecules with less complex structures have a comparative advantage over the most functionally potent aptamers because oligomers with 'simple' structure replicate more efficiently (Klug and Famulok, 1994).

SUMMARY OF INVENTION

The present invention features methods, compositions, kits, and apparatus for determining the presence or absence of a target molecule.

One embodiment of the present invention is a composition. The composition comprises a first ribonucleic acid (RNA) molecule and a second RNA molecule. The first RNA molecule is capable of binding to a target molecule and has the following formula:

As used above, A is a section of the RNA molecule having 10-100,000 nucleotides, which section is capable of being received by an RNA replicase and with another RNA sequence, F, being replicated. The letter "B" denotes a section of the RNA molecule having approximately 10 to 50,000 nucleotides, which section is capable of binding to the target molecule. The letter "C" denotes a section of the RNA molecule having approximately 1 to 10,000 nucleotides which section is capable of being ligated to another RNA sequence, "D". The second RNA molecule is capable of binding to a target molecule and has the following formula:

As used above, D is a section of the RNA molecule having approximately 1 to 10,000 nucleotides, which section is capable of being ligated to another RNA sequence, "C". The letter "E" denotes a section of the RNA molecule having approximately 10 to 50,000 nucleotides, which section is capable of binding to the target molecule. The letter "F" denotes a section of the RNA molecule having 10–100,000 nucleotides which section is capable of being received by an RNA replicase and with another sequence, "A", being replicated. The first and the second RNA molecules are capable of forming a third RNA molecule having the following formula:

5'-A-B-C-D-E-F-3'.

The third RNA molecule is formed by ligation the C and D sections, as the E and the B sections are bound to the target. The third RNA molecule is capable of being received by an RNA replicase and being replicated by such enzyme.

Preferably, the sequences represented by the Letters "A" and "F" are selected from the group of sequences consisting of MDV-I RNA, Q-beta RNA microvariant RNA, nanovariant RNA, midivariant RNA and modifications of such sequences that maintain the ability of the sequences to be replicated by RNA replicase. Preferably, the replicase is Q-beta replicase.

Preferably, the sections B and E each are sections having 10–5,000 nucleotides and, even more preferred, 20–50 nucleotides. Preferably, the sections B and E bind to the target through non-nucleic acid base pairing interactions. And, most prefered, the B and E sections are aptamers or partial aptamers as defined by Klug and Famulok (1994). Aptamers are selected for a particular functionality, such as binding to small or large organic molecules, peptides or proteins, the tertiary structure of nucleic acids or complex or simple carbohydrates.

Preferably, the sections C and D each have 1–10,000 nucleotides, and more prefered, 1–1000 nucleotides, and most prefered, 1–15 nucleotides. Preferably, the sections C and D, when ligated together, define a recognition site for a ribozyme or a target of another compound that has an endonucleolytic activity against a single-stranded nucleic acid.

A further embodiment of the present invention features a method of determining the presence or absence of a target molecule. The method comprises the steps of providing a first RNA molecule and a second RNA molecule. The first RNA molecule is capable of binding to a target molecule and has the formula:

5'-A-B-C-3'.

The sections A, B and C are as previously described. The second RNA molecule is capable of binding to the target molecule and has the formula:

5'-D-E-F-3'.

The sections D, E and F are as previously described. The method further comprises the step of imposing binding conditions on a sample potentially containing target molecules in the presence of the first and second RNA molecules. In the presence of the target molecule, the first and the second RNA molecules form a complex with the target molecule. The method further comprises the step of imposing RNA ligase reaction conditions on the sample to form a third RNA molecule in the presence of the target. The third RNA molecule has the formula:

5'-A-B-C-D-E-F-3'.

The sample is monitored for the presence of the third RNA molecule, presence or absence of which is indicative of the presence or absence of the target molecule.

Preferably, the sections B and E bind to the target through non-nucleic acid pairing interactions. And, most prefered, the B and E sections are aptamers or partial aptamers.

Preferably the sections C and D together comprise 5–15 nucleotides which define a site for a ribozyme or a target of another compound that has endonucleolytic activity against a single-stranded nucleic acid.

Preferably, at least one of the first or second RNA molecules has a signal generating moiety. After RNA ligase reaction conditions are imposed, the method preferably comprises the further step of separating or enzymatically destroying the RNA, molecules unbound with the target molecule and bearing the signal generating moiety.

Preferably, the signal-generating moiety is sections A and F of the third RNA molecule, which sections allow recognition and replication by RNA replicase. Thus, the method further comprises the step of imposing RNA replicase conditions on the sample potentially comprising the third RNA molecule.

A further embodiment of the present invention comprises a kit for determining the presence or absence of a target molecule. The kit comprises one or more reagents comprising a first RNA molecule, a second RNA molecule and an RNA ligase. The first RNA molecule has the formula:

5'-A-B-C-3'.

The second RNA molecule has the formula:

5'-D-E-F-3'.

In the presence of the target, the first and the second RNA molecules are capable of forming a target-first-and-second-RNA complex and in the presence of RNA ligase means forming a third RNA molecule having the formula:

5'-A-B-C-D-E-F-3'.

The letters A, B, C, D, E, and F are as previously described. The third RNA molecule is preferably capable of being received and replicated by RNA replicase.

Preferably, the kit further comprises reverse transcriptase and suitable primers.

An embodiment of the present invention further comprises a method of making a first RNA molecule and a second RNA molecule, wherein the first RNA molecule has the formula:

5'-A-B-C-3' and the second RNA molecule has the formula:

5'-D-E-F-3'.

As used above, the letters A, B, C, D, E, and F are as previously described, and the sections C and D together define a site for cleavage by ribozyme or another compound having endonucleolytic activity against a single-stranded nucleic acid.

The method comprises the step of combining a sample containing the target molecule with a library of RNA molecules having the formula:

5'-A-B'-C-D-E'-F-3' to form a mixture of one or more target bound-RNA molecules and one or more unbound-RNA molecules. The letters B' and E' represent potential sections B and E.

Preferably, the sections B' and E' are randomized nucleotides.

Next, primer nucleic acid corresponding to at least one section is added to the mixture with an enzyme capable of degrading the unbound RNA molecules. Next, bound RNA molecules are released from the target and amplified with RNA replicase, and preferably Q-beta replicase, to form an amplification product. Next, the RNA molecules comprising the amplification product having the formula:

5'-A-B'-C-D-E'-F-3' are cleaved to form the first and second RNA molecules.

Preferably, the cleavage is performed with a ribozyme or other endonucleolytic enzyme and the sections C and D together define a cleavage site for the ribozyme or another endonucleolytic enzyme.

Preferably the step of degrading the unbound RNA molecules is performed in the presence of the enzyme reverse transcriptase. Preferably, the step of amplifying the bound RNA molecules is performed in the presence of the enzyme Q-beta replicase.

An embodiment of the present invention further comprises a kit for performing the above method of identifying first and second RNA molecules. The kit comprises one or more nucleic acid molecules having sections corresponding to the sections A, B, C, D, E, and F. Preferably, the kit comprises sections B' and E' as randomized nucleotide sequences.

As used herein the term "kit" refers to an assembly of parts, compositions and reagents with suitable packaging materials and instructions.

The present invention is further described in the following figure and examples, which illustrate features and highlight preferred embodiments and the best mode to make and use the invention.

DETAILED DESCRIPTION OF INVENTION

Figure 1:
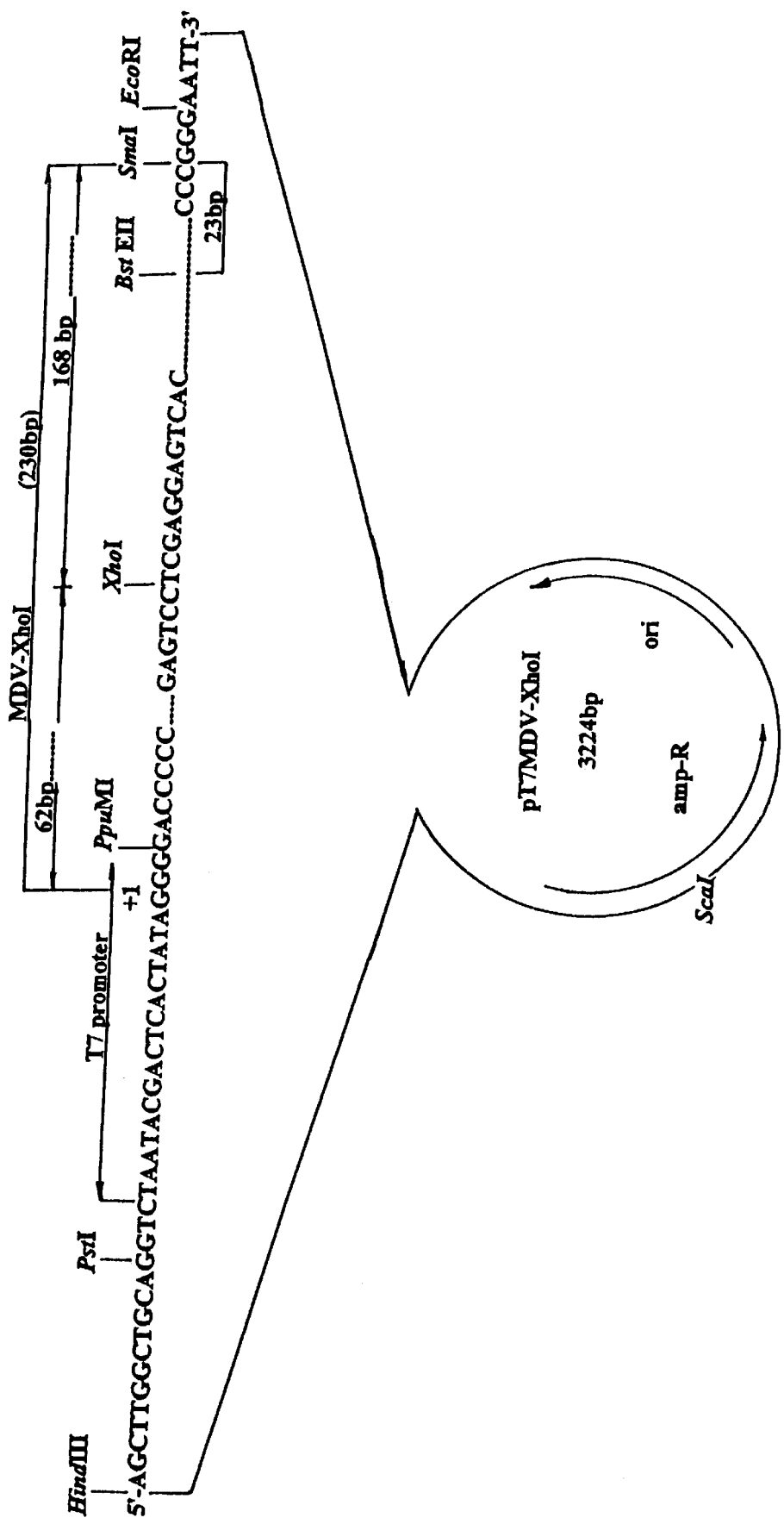
FIG. 1 depicts plasmid pT7 MDV-XhoI. This plasmid was used for cloning synthesized PX and XS dsDNAs and for the transcription of the PX and XS recombinant RNA molecules that served as detector molecules for adenovirus sequences. This plasmid is a variant of the parent plasmid, pT7 MDV, in which the XhoI linker sequence is not present. For further details of the construction of the vector, see Axelrod et al., 1991

The present invention will be described with respect to a SELEX process and Q-beta technology. The method features the incorporation of specially-designed RNA libraries into a Q-beta replicase template. The methods of the present invention are more effective than other methods known in the art for several reasons.

First, Q-beta replicase can only use templates with high structural complexity, which are the best candidates for aptamers with great affinity for the target molecule. The original library will be pre-selected for the species with secondary and tertiary structures when the original library of randomized sequences is amplified with Q-beta replicase prior to its contact with the target molecule.

Secondly, the special design of the libraries will allow amplification of the high affinity ligands by enzymatic degradation of the low affinity molecules discriminately and selectively without an elaborate process of partitioning them from ligands of low affinity.

Thirdly, amplification of the ligands by Q-beta replicase as a part of the chimeric template RNA seems more manageable technically and more time advantageous than using routine PCR techniques during standard SELEX procedures.

Finally, Q-beta chimeric RNA template with an insert of RNA ligands highly specific for a target protein can serve directly as a unique tool to detect in clinical specimens target molecules having tertiary configurations.

The method of the invention has application for constructing specially designed nucleic acid detector molecules for any analytes, including proteins, that naturally exhibit an affinity for nucleic acid molecules and, especially, RNA molecules. The methods, compositions and kits have utility in the study of RNA-protein interactions arid their significance in regulatory systems, for diagnosis of cancer, infectious and inherited diseases. The list of naturally-occurring and medically-important RNA-protein complexes includes, but is not limited to, RNA-binders of bacteria and parasites, intron binding proteins, RNA epitopes in autoimmune diseases, protein-nucleic acid complexes of spinal muscular atrophy or in fragile-X mental retardation and RNA-protein subunits in telomerase. Naturally occurring nucleoprotein complexes also include any regulatory proteins, enzymes, antibodies, antibiotics and other complex chemical compounds, as well as simpler complexes, such as nucleotides, nucleosides or amino acids and such, for which naturally-occurring nucleic acid ligands have been identified and described. The proposed method is also useful for any target molecule for which nucleic acid ligands were obtained through SELEX, in vitro selection or in vitro evolution procedures.

The embodiments of the present invention feature a method for constructing the sets of two detector molecules for identifying various analytes different from nucleic acid targets in a specimen. The composition of the detector molecules is based on a ligand's nucleotide sequences, and the secondary and tertiary structure of the ligand corresponds to such target analyte. The detector molecules mean two RNA molecules that serve triple purpose: to be a ligand with high affinity to the target analyte, to be ligated into one functional molecule, and to be a template that could be amplified by Q-beta replicase after its ligation by RNA ligase. The specimen means any sample taken from any source and representing the source. Target analyte means any compound of interest without limitations. Ligand means a nucleic acid molecule that demonstrates high affinity to the target analyte.

One embodiment of the present invention features a method for designing and constructing two detector molecules representing the nucleic acid component of a nucleoprotein complex molecule or a ligand of known nucleotide sequence, which will be constructed through cloning them as appropriate oligonucleotides in the recombinant plasmid using a Q-beta replicase template cDNA insert or synthesizing them on a DNA synthesizer, or using PCR techniques.

To construct the detector molecules for a target analyte with a known ligand, two sets of complementary oligonucleotides are designed and synthesized on a DNA synthesizer. One set of oligonucleotides is dsDNA representing the 5' part of the whole ligand. The other set of oligonucleotides is dsDNA representing the 3' part of the same ligand. Both dsDNAs are designed with terminal restriction enzyme sites for cloning in the vector, and with additional nucleotides with lengths from one to ten nucleotides. These additional sequences will be used in subsequent steps of the procedure to synthesize captomers (from Lat. captere—seek to get), parts of the molecules with a specially-designed fiinction. The first dsDNA has the following formula: M-N-O-P. The second dsDNA has the following formula: P-R-S-T, where M, P and T are restriction site linkers, O is sequences representing the 5' segment of the ligand, R is sequences representing the 3' segment of the ligand, and N and S are the sequence with donor and acceptor termini employed in a ligation reaction.

These two dsDNAs are cloned in a recombinant plasmid containing T7 RNA promoter, followed immediately by inserting a Q-beta replicase template cDNA (FIG. 1). Three unique restriction sites (M, P and T) for cloning dsDNA molecules are incorporated into the recombinant plasmid. One cloning site, M follows the T7RNA promoter immediately. The T cloning site is inserted into the end of the Q-beta replicase template, and the P site divides the template insert into two, 5' and 3',parts. Thus, the 5' part of the Q-beta replicase template is flanked by M and P restriction sites and 3' part of the template is flanked by P and T restriction sites.

The composition of the insert in such recombinant plasmid will be:

T7 promoter-M-Q-beta template-P-Q-beta template-T

A second recombinant plasmid is prepared by replacing the 5' part of the Q-beta replicase template cDNA situated between the M and P restriction sites with corresponding dsDNA representing the 5' segment of the ligand. The combined insert of the second recombinant plasmid has the following formula:

T7 promoter-M-N-O-P-Q-beta template-T.

A third recombinant plasmid is prepared by replacing the 3' part of the Q-beta replicase template cDNA situated between the P and T restriction sites with corresponding dsDNA representing the 3' segment of the ligand. The combined insert of the third recombinant plasmid has the formula:

T7 promoter-M-Q-beta template-P-R-S-T.

Recombinant plasmids containing the template sequences with the sequences inserted from the original DNA library are used to transform competent bacterial cells, and the transformed cells are grown in a culture. The cultured cells are harvested and lysed. The DNA plasmids are purified. In the said method for design and construction of the first and second detector-molecules, the recombinant plasmids are cleaved with an appropriate restriction enzyme and the recombinant Q-beta replicase templates containing the inserts are transcribed into the RNA using T7 RNA promoter. All procedures are performed according to the standard protocols of J Sambrook, E F Fritsch and T Maniatis (1989) known to someone skilled in the field of molecular biology.

The second and third recombinant plasmids will be linearized by cleavage in the T restriction site, and the recombinant RNAs will be transcribed from each plasmid using the T7 RNA promoter.

Two recombinant RNA transcripts are the set of detector-molecules for the chosen analyte.

Each such RNA detector-molecule consists of three segments.

The structure of the first detector-molecule is:

5'-A-B-C-3'.

And the structure of the second detector-molecule is:

5'-D-E-F-3'.

Each component has one defined function—amplification, recognition or ligation. The A and F 'amplification' segments of the first and second detector-molecules are parts of a template replicable by Q-beta replicase. The nucleotide composition and the length of the A and F segments depends on the replicable RNA they represent. Preferably, segments A and F are selected from the group of replicable RNAs consisting of MDV-I RNA, Q-beta RNA, microvariant RNA, midivariant RNA, nanovariant RNA, or modifications thereof that permit the RNA to maintain its reproducibility. Neither the A nor the F parts of the Q-beta template can separately serve for amplification by Q-beta replicase.

The B and E 'recognition' segments represent the full length or part of two ligands with high affinity to two epitopes of the same analyte, or, they are two parts of a s;ingle nucleic acid ligand with high affinity to a single epitope of the target analyte or nucleic acid component of the nucleoprotein complex. Segments B and E are the RNA transcripts of the R and O parts of the ligand described above.

The D and C 'ligation' segments termed captomers (from Lat. captere—seek to get) are segments of the detector molecules, with specially-designed donor and acceptor terminal nucleotides that are essential for ligating the two detector molecules after they bind with the target molecules, the termini of which are used by RNA ligase in the ligation reaction to form phosphodiester bonds. The lengths of these segments can be as short as one nucleotide and as long as 10,000 nucleotides. These two segments are the R:.NA transcripts of the captomer parts N and S of the recombinant dsDNA molecules. Neither of these two recombinant RNA molecules can separately serve as a template for Q-beta replicase.

The synthesis of dsDNA, the cloning and the transcription of the recombinant RNA molecules are performed under the conditions described in detail (Sambrook et al., 1989) and known to someone skilled in the field of molecular biology.

Another embodiment of the present invention features a method for designing and constructing a pair of detector-molecules for any three-dimensional analyte when the nucleotide sequence of its ligand is not known. The method comprises the steps of providing a first detector-molecule and a second detector-molecule.

Preferably, the process starts from constructing machine-synthesized libraries of deoxyribooligonucleotides. Each member of each library is composed of at least the four segments: 5'-B-CD-E-X-3',where the B and E segments are approximately 10–50,000 nucleotides and, most preferably, 20–50 nucleotides each, and the CD segment is of 1 to 10,000 nucleotides and, most preferably, 2–30 sequences, and X is 10–15 nucleotides long.

Preferably, the B and E segments are random nucleotide sequences where A, T, C and G nucleotides have an equal probability to be incorporated in any position of the segment. Each member of the synthesized library is different from others in these two regions.

Preferably, the CD segment contains DNA sequences that are a recognition site for a known ribozyme defined and described by O. Uhlenbeck (1987) as well as by G F Joyce (1989), T R Cech, F L Murphy, A J Zaug, C. Grosshans, U.S. Pat. No. 5,116,742 (1992), J P Hazeloff, W L Gerlach, P A Jennings, F H Cameron, U.S. Pat. No. 5,254,678 (1993), H D Roberson and A R Goldberg U.S. Pat. No. 5,225,337 (1993) or any other compound that demonstrates a specific endonucleolytic activity with single-stranded nucleic acid molecules. The segment with ribozyme recognition sequences is identical in all molecules of the same library, but varies among the libraries.

Preferably the X segment is a DNA oligonucleotide segment with random, but defined sequences. Each molecule of the synthesized library has the same X region.

The single-stranded original library will be converted into a double-stranded DNA library using any DNA polymerase that includes, but is not limited to DNA polymerase I, Kienow fragment, T4 DNA polymerase, T7 DNA polymerase, and primers complementary to the X section of the synthesized molecules. The conversion of the ssDNA library into a dsDNA library, primer and enzymes is performed under standard conditions known to someone skilled in the field of molecular biology.

The dsDNA library is cloned into a recombinant plasmid (similar to the one described previously, FIG. 1) containing the T7 RNA transcription promoter attached to a cDNA copy of the Q-beta replicase template with an insert of a unique restriction enzyme linker within the sequence of whole recombinant plasmid, including the Q-beta replicase template. Insertion of the library sequences into the Q-beta template at the position chosen must not unduly perturb the features of the template necessary for successful amplification. Insertion of the dsDNA library into a recombinant plasmid containing a cDNA copy of Q-beta replicase template is performed under standard conditions known to someone skilled in the field of molecular biology.

Recombinant plasmids containing the template sequences with the inserted sequences from the original DNA library are used to transform competent bacterial cells, and the transformed cells are grown in a culture. The cultured cells are harvested and. lysed. The DNA plasmids are purified. In the said method for design and construction of the first and second detector-molecules, the recombinant plasmids are cleaved with an appropriate restriction enzyme and the recombinant Q-beta replicase templates containing the inserts of the original DNA library are transcribed into the RNA library using T7 RNA promoter. All procedures are performed according to the standard protocols of Sambrook et al., (989) known to someone skilled in the field of molecular biology.

Composition of each species of the second RNA transcripts library, is 5'-A-B-CD-E-F-3'. Each species is a molecule with three functional parts: A and F are two parts of a single Q-beta template and they enable amplification of the whole detector molecule. The B and E segments represent random sequences of the library in the recombinant RNA transcript. The CD segment of each RNA transcript is a joining region of the B and E sequences and contains a recognition site for a chosen ribozyme or any other compound that demonstrates the cleavage of the single-stranded nucleic acid-specific sequences. The X segment is not essential for further procedures and it is not considered in further description.

A further embodiment of the present invention describes a method of enrichment of the original RNA library with RNA species that demonstrate secondary and tertiary complexity in the B and E regions. The recombinant transcript-RNAs' library templates are used to initiate amplification in a standard Q-beta replicase reaction according to the standard procedure described in detail by Axelrod et al., (1991). The secondary structure of the RNA templates has a very powerful influence on replication by the Q-l)eta enzyme. In fact, the existence and continual propagation of whole recombinant RNA species as self-replicating entities depends on these structures as the major factor in determining the viability of the amplification products. Q-beta replicase discriminates the inserts as a part of the template molecule on the basis of their secondary structures and provides a positive selection favoring those templates containing inserts with more complex secondary structures, as follows from Axelrod et al., (ibid). Thus, after several, preferably three or four, cycles of replicating with Q-beta replicase, the library of recombinant RNA templates will be 'preselected' for those recombinants with a higher proportion of the complex secondary structures that result from nucleotide pairing and interaction.

Additionally, the 'preselection' process for spatial complexity of B and E region will lead to an additional diversity of the original RNA library. Since Q-beta replicase can use both, plus and minus strands of RNA as templates, the 'preselected' library will consist of two types of molecules that are plus and minus versions of the same sequence.

The secondary structure motifs contain such elements as pseudo knots, simple stems or hairpins, or stems with loops, or symmetrical and asymmetrical bulges and such. Double-stranded RNA of the B-CD-E part with motifs of secondary structure in turn form a three dimensional structure, the tertiary structure of the recombinant RNA in this region, converting the B and E segments into segments with randomized three-dimensionally-structured nucleotide sequences. The relationship between nucleotide sequences in RNA molecules, and secondary and tertiary organization of RNA molecules is described in detail by L. Gold and C. Tuerk, U.S. Pat. No. 5,475,096 (1995).

The further embodiment of the present invention features a procedure for selecting recombinant RNA species that demonstrate high affinity to a target molecule of particular functionality, such as binding to small or large organic and non-organic molecules with their own tertiary structures, including peptides or proteins, nucleic acid molecules or oligonucleotides, nucleotides or amino acids, complex or simple vitamins, antibiotics and carbohydrates and such without limitation. The procedure comprises the steps of contacting the library with the target molecules, providing an annealing of the detector-molecules preselected for tertiary structure with a population of the said target molecules under conditions favorable for forming the complex between the chosen target and recombinant RNA molecules. The annealing will be performed under favorable conditions described by Gold et al., (1995) and known to someone skilled in the art of molecular biology. Specifically, the recombinant RNA molecules will form a binding complex with the target molecule in the 5'-B-CD-E-3' region, and particularly, in the B and E segments. Preferably, sections B and E bind through non-nucleic acid base pairing interaction to the analyte. These two segments may anneal to the same 'epitope' of the target molecule, acting as two parts of a single nucleic acid ligand or, as an alternative, the B and E segments can act as two separate ligands forming bonds with two separate 'epitopes' of the same target molecule. The CD region may or may not participate in the annealing with the target molecule, depending on its nucleotide constitution, nature of the target molecule and its interaction with the B and E segments.

Several possible configurations of molecules are in the mixture after completing an annealing reaction: free RNA species, free target molecules and RNA/target molecule complexes. Additionally, RNA/target molecules complexes can be formed by annealing both B and E segments to the analyte molecules, or either of them, B or E, annealed to the analyte molecule separately. Several methods suggested for partitioning the free RNA species from the target/RNA complexes, including filter binding, gel mobility shift, affinity chromatography, antibody precipitation, phase partitioning and protection from nucleolytic cleavage by catalytic RNAs, termed ribozymes, have been described in detail by L. Gold and C Tuerk, U.S. Pat. No. 5, 475,096 (1995). Further, L. Gold and S. Rinquist, U.S. Pat. No. 5,567,588

(1996) widened the methods that should be employed for partitioning nucleic acid molecules annealed to the target analyte from those that do not bind the target molecules. Their new method, termed solution SELEX, employs a primer extension inhibition, exonuclease hydrolysis inhibition, linear to circlular formation, and single stranded nucleic acid PCR amplification for the partitioning between high- and low-affinity nucleic acid-target complexes.

A further embodiment of the present invention is based on the enzymatic selection of the recombinant RNA template with high affinity to target molecules of the B-CD-E region embedded between two sectors, A and F, of the Q-beta template. To initiate this selection, we use a reverse transcriptase (RT), preferrably Avian myeloblastoma virus (AMV) reverse transcriptase and an RT primer with nucleotide sequences complementary to a segment of CD region. Reverse transcriptase from avian myeloblastosis virus is a DNA polymerase that catalyzes polymerization of nucleotides using an RNA template. This enzyme consists of two polypeptide subunits, one of which contains 5'-3' polymerase activity and the other a powerful RNase H activity (Verma, 1991). Reverse transcriptase has been widely used to synthesize complementary DNA (cDNA). Such synthesis requires a primer and free nucleotides. The RT enzyme will synthesize cDNA and simultaneously degrade the complementary RNA molecule because of its RNase H activity. RNA with high affinity to the target analyte molecule will be protected from degradation due to the fact that the primers do not bind and RT cannot synthesize cDNA. Therefore RNase H has no activity.

The dissociation constant of the high affinity detector RNA-target analyte complex is in the nanomolar-or-less range and efficiently inhibits annealing of the primer with complementary sequences of the C and D regions bound to two separate epilopes or with one epitope, and, possibly, in configuration when only the C or D region is bound to a single epitope. The success of the RT primer annealing with the RNA molecule in the latter configuration will depend on the energy balance between the epitope-RNA and the primer-RNA complexes. At the same time, the RT primer will anneal efficiently with the complementary sequences of the CD region of the free recombinant RNA molecule. As a result, reverse transcriptase synthesizes the cDNA strand using the free recombinant RNA molecule only, and in those RNA-target complexes where the energy balance shifts in a direction favorable for creating a primer-RNA complex. In the process of synthesizing cDNA, reverse transcriptase degrades the original RNA in RNA-DNA hybrids exonucleolytically because it has RNase H activity. Thus, a large section of the recombinant RNA molecules with low affinity to the target, starting from the CD section to the end of the whole RNA recombinant molecule will be degraded. As a result, all low affinity and partially annealing to the analyte RNA molecules will be eliminated from the amplifiable pool, and only completely annealing with target analyte recombinant RNA molecules with high affinity for the B-CD-E region will represent the pool amplifiable by a Q-beta replicase template.

Using enzymatic degradation of RNA molecules with low affinity to the target by RNase H allows isolation and consequent dissociation of the high affinity RNA-target molecules complex and purification of the high affinity RNA molecule(s) from the target molecules. Purification of the whole-length recombinant RNA molecules from the target is performed in conditions favorable for each target-RNA molecule combination. Purified RNA recombinant molecules with high affinity to the target are amplified by Q-beta replicase, using the standard protocol described further in the EXAMPLE section.

A further embodiment of the present invention features the procedures for producing detector molecules from the product of the described ezymatic degradation of low affinity RNA species and propagation of recombinant RNA molecules that demonstrate high affinity to the chosen target analyte. All members of the remaining population will be exposed to an appropriate ribozyme or another agent that specifically cleaves; the CD sequence. Each RNA molecule will be split into two molecule-detectors. The first moleculedetector will be composed of the sectors 5'-A-B-C-3'. The second molecule detector will have the order of the segments comprising it as 5'-D-E-F-3'. The function of each segment was described earlier, except that each of the detector molecules will have a new component—a terminal C or D region that was previously united in the CD region of the transcribed recombinant RNA molecule. These two regions acquire a new important function in the detectormolecules and will serve as the donor-acceptor captomers, the parts of the ligation complex.

The constructed set of two detector molecules is ready for use in detecting target analytes in clinical specimens.

In a modified variant, the detector molecules are ssDNA molecules with the composition of the segments similar to those of the RNA nature. Both detector molecules contain the sequences representing the two parts of the Q-beta replicase template, the detection parts with high affinity to the analyte molecule and the sequences recognizable by a DNA endonuclease. One of the detector molecules further inclides an RNA polyrnerase promoter sequence to enable transcription of the DNA detector-molecules anmealed to the target and ligated into a recombinant RNA molecule. The organization of such recombinant RNA is the same as was desribed previously, that is, restriction enzyme sequences are flanked by two analyte recognition sequences and those sequences are flanked by Q-beta replicase template sequences. This recombinant RNA molecule is a template that will be amplified by Q-beta replicase.

A further embodiment of the present invention features the procedures for detection of an analyte molecule in a specimen using a constructed set of detector molecules. The constructed detector molecules could be used in diagnostic tests, in diagnostic test kits and for microsensors or nucleic acid biochip production. For detection of an analyte molecule, a mixture of two detector-molecules is combined with a specimen potentially containing the target analyte. The target, when present in the specimen, will bind the detector-molecules, and the two halves of the original recombinant RNA molecule will be situated on the target analyte in such a position that they can be ligated with RNA ligase. After ligation, which occurs between the 3' and 5' terminal nucleotides of the C and D sectors, the two detector molecules form a single molecule. Such molecules that combine the A and F sectors of the detector molecules, can serve as a template for Q-beta replicase. Template ability is restored after ligation of the detector molecules into a single reporting recombinant template molecule that can then be amplified by Q-beta replicase.

In the previously desribed work, the integrity of one of the templates for Q-beta replicase MDV-I RNA was restored by T4 DNA ligase from the two detector-molecules after their simultaneous annealing to the target nucleic acid molecule (Martinelli et al., 1 995, Tyagi et al., 1996). To join the detector probes into a single molecule, the authors used T4 DNA ligase because this enzyme requires (1) that two detector molecules will form with the target molecule a 'double stranded DNA complex' and (2) that this detector molecule-target complex will demonstrate a 'certain rigidity in its structure' (quotes from Martinelli et al., 1995 and Tyagi et al., 1996). The importance of the double-stranded DNA complex and its configuration for successful ligation follows from the mechanism of the reaction catalyzed by DNA ligase, described in detail by Engler and Richardson (1982).

DNA ligase cannot be applied for ligation of the detectormolecules in an assay where proteins or other than nucleic acid analytes are used as targets, because there is only one nucleic acid strand in the ternary complex represented by the nucleic acid detector-molecules. Secondly, interaction of the analyte and nucleic acid ligand in the complex is not so 'tight' or 'rigid' as the nucleic acid probe-target in the hybridization complex. Such 'loose' interaction of the analyte and detector-molecules prevent DNA ligase from joining two detector molecules covalently into a single molecule.

As an alternative, we claim use of another enzyme for joining the two RNA detector-probes when they bind targets other than nucleic acid. One such enzyme can be RNA ligase, and preferably T4 RNA ligase, originally described by Leis et al., (1972). Similarly to DNA ligase, T4 RNA ligase catalyzes the formation of a 3'→5' phosphodiester bond between a 3'-terminal hydroxyl and a 5'-terminal phosphate of polyribonucleotides with hydrolysis of ATP to AMP and Ppi (Silber et al., 1972). The circularization reaction of the oligonucleotides by T4 RNA ligase provides some information on the optimum physical distance between the donor and acceptor parts of an RNA molecule, the optimum of which varies between a distance of 10–16 nucleotides (Kaufmann et al., 1974, Sugino et al., 1977). The major feature that differs RNA ligase from DNA ligases is that RNA ligase aligns the free ends of the reacting donor and acceptor on its surface, whereas DNA ligase requires a base-paired template that fixes the oligonucleotide ends in close proximity (Engler and Richarson, 1982, Uhlenbeck and Gumport, 1982).

To create the optimal condition for the RNA ligase, the claimed set of detector-molecules is designed with the option to bind the target analyte with a gap between them. Additionally, each of the detector-molecules is designed with terminal nucleotides that should be free in a detector-analyte complex. Neither of these new structural components in the claimed detector-target complexes exists in standard nucleic acid probe-nucleic acid target complexes.

Using the specifics cited above in the RNA ligase action and the specially-designed detector-molecules, we claim an application of RNA ligase, and preferably T4 RNA ligase, to ligate two RNA molecules when they form a ternary complex with any non-nucleic acid target, or when RNA molecules form a ternary complex with a target molecule structurally similar to those that formed with the nucleic acid target. Preferably the RNA molecules do not align contiguously with each another on the nucleic acid target or on the analyte forming a gap between 20 and 200 angstroms. Additionally, the RNA molecules align on the nucleic acid target or on the analyte with free termini, that do not hybridize to the target nucleic acid molecule or bind to the analyte.

Overall, we claim to use three principal novelties that allow us to extend application of the designed detector-molecules for any analyte targets including other than nucleic acids: They are:

the captomers make the detector-molecules accessible to be joined covalently into one molecule the detector molecules form a ternary complex with a target analyte molecule that is structurally suitable for RNA ligase RNA ligase assembles and aligns the free ends of the reacting captomers on its surface and restores the ability of the Q-beta template to serve as a template for amplification Another embodiment of the present invention is the composition of the two detector-molecules that work in conjunction with each other when they are used in diagnostic protocols, kits or apparati. Each of the detector-molecules consists of three functional parts. One of them is a segment of Q-beta replicase template, another is a segment of the sequence with high affinity to the target, and the third part is a segment of the sequences with the recognition site for a chosen endonucleatic compounds which, after the cleavage, acquires a captomer's function. The first detector molecule is capable of binding to the target molecule and has the following formula, with at least three components organized in a 5'→3' direction as:

5'-A-B-C-3'.

As used above, A is a section of the first detector molecule having the 5' section of a Q-beta replicase template, which is not capable of binding to the target molecule and which is not capable of replication. The letter B denotes a section of approximately 20 to 50 nucleotides of the first detector-molecule which is the section capable of binding to the target molecule. The letter C denotes a captomer, a section of the first detector composed of approximately 1 to 15 nucleotides, which is the primary substrate for a rib)zyme. The C captomer can and cannot be capable of binding to the target molecule.

The second detector-molecule is capable of binding to the target molecule and has the following formula with at least three components organized in a 5'→3' direction as:

5'-D-E-F-3'

As used above, the letter D denotes a captomer, a section of the second detector composed of approximately 1 to 15 nucleotides, which is another primary substrate for a ribozyme. The D captomer can and cannot be capable of binding to the target molecule. The letter E denotes a section of the second detector-molecule having approximately 20 to 50 nucleotides which section is capable of binding to the target molecule in the same 'epitope' as sector B of the first detector molecule or to its own 'epitope'. The F part of the second detector-molecule contains the remaining 3' section of a Q-beta replicase template. The A and F segments are not capable of binding to the target molecule and cannot be amplified separately by Q-beta replicase.

Preferably, sections C and D are the nucleotide sequences, termed captomer, that can serve as a donor, since section C naturally terminates in the hydroxyl group required for ligation, and, section D, that can serve as an acceptor, with a terminal monophosphate group required by the ligation reaction catalyzed by RNA ligase, which includes but is not limited to bacteriophage T4 DNA ligase. The ligation reactions are performed under standard conditions known to those skilled in the field of molecular biology.

Preferably, upon ligation of sections C and D the two detector-molecules form a single molecule composed of five parts in the 5'–3' order

5'-A-B-C-D-E-F-3' as in the original recombinant RNA demonstrating high affinity to the target molecule.

Preferably, the newly formed molecule is a template amplifiable by Q-beta replicase and has a signal-generating moiety. Signal-generating moieties comprise, by way of example, radiolabeled nucleotides, enzymes, ligands, fluorescent or chemoluminescent agent, or sequences of nucleotides capable of detection. A preferred signal-generating moiety is section A of the first detector molecule and section F of the second detector-molecule, which are two sections of the replicable nucleic acid template. And, most preferably, sections A and F are selected from the naturally-occurring group of replicable RNAs consisting of MDV-I RNA, Q-beta RNA, microvariant RNA, midivariant RNA, nanovariant RNA and modifications thereof, or any artificially constructed RNA templates that permit the RNA to maintain replicatable RNA. In the presence of the enzyme Q-beta replicase and suitable reaction conditions, preferred replicatable RNAs are produced and act as a signal that such replicatable RNA is present initially as sections A and F in the two detector-molecules and the reaction product in which it is incorporated.

A further embodiment of the present invention features a method of determining the presence or absence of a target molecule. The method comprises the steps of providing first and second detector-molecules. The first detector-molecule is a non-naturally occurring, recombinant RNA molecule capable of binding to a target analyte and has a structure

5'-A-B-C-3'.

The segments A, B and C are as previously described. The second detector molecule is a non-naturally occurring, recombinant RNA molecule capable of binding to the target analyte and has a structure:

5'-D-E-F-3'.

The sections D, E, F are previously described.

The method further comprises the step of imposing binding conditions on a sample potentially containing target molecules in the presence of the first and second detector-molecules. In the presence of the target molecule, the first and second detector molecules form a target first and second detector-molecule complex. The method further comprises the step of imposing RNA ligase reaction conditions on the sample to form a third RNA molecule in the presence of the target analyte. The third RNA molecule has the formula:

5'-A-B-C-D-E-F-3'.

The sample is monitored for the presence of the third RNA molecule, whose presence or absence indicates the presence or absence of the target analyte molecule.

Preferably, sections B and E bind to the target analyte through non-nucleic a(cid pairing interactions. And, most preferred, B and E are ligands demonstrating high affinity to separate epitopes of the same target analyte or they are parts of the same ligand that demonstrates high affinity to a single epitope of the target analyte.

Preferably, sections C and D are capable to serve as donor and acceptor captomers in the ligation reaction and can join covalently at the respective termini by the action of RNA ligase.

Preferably, at least one of the first or second detector-molecules has a signal-generating moiety. Preferably, the non-signal-generating first and second detector-molecules are ligated and comprise a functioning, signal-generating template that can be amplified by Q-beta replicase. The analyte and the third RNA molecule are associated in the complex. All procedures of the binding of detector and analyte molecules and ligation of the detector molecules are performed according to the standard protocols known to the someone skilled in the art of molecular biology.

A further embodiment of the present invention features the procedures essential for the elimination of possible background. The method preferably comprises the further step of hybridization of a specially designed primer with the complementary region of the C section prior to the template's amplification by Q-beta replicase. For this hybridization, the mixture of detector-molecules annealed and non-annealed to the analyte are mixed with the primer that has complementary nucleotide sequences and can bind to a segment of the CD region of the ligated product. The mixture will be exposed to favorable conditions under which the primer will be reassociated with the complementary sequences of the CD region.

After primer reassociation conditions are imposed, the method preferably comprises the further step of enzymatic degradation of the template molecules resulting from ligation of the first and second detector-molecules without binding to the analyte. Such molecules still bear the signal-generating moiety and, therefore, could be the source of background and false positive results. For this, the mixture will be exposed to AML reverse transcriptase as was described earlier. Similarly, the enzyme with its dual function will synthesize cDNA complementary to the CD, E and F, or A and B regions depending on the plus or minus nature of the ligated product, and will simultaneously degrade these segments of the RNA template, eliminating the 5' portion of those template molecules not forming a complex with the target analyte.

After enzymatic degradation of the detector-molecules that are the ligation products of the first and second detector-molecules in the absence of the target analyte, the remaining templates are exposed to amplification by the Q-beta replicase enzyme.

A further embodiment of the present invention comprises a kit for determining the presence or absence of target molecules. The kit for identifying specific analytes in a specimen is composed of one or more reagents comprising the first and second detector-molecules specific for the desired or target analytes, RNA ligase, AML reverse transcriptase, Q-beta replicase, primer for the reverse transcriptase, and buffers, salt and reagent solutions necessary to perform the experiments according to the designed protocol. The first detector molecules have the formula:

A-B-C.

The second detector molecules have a formula:

D-E-F.

All segments of the detector molecules are previously described.

A universal kit for constructing the detector molecules for any analyte of interest may be composed of one or more reagents comprising one of the RNA libraries, each species in which has a formula:

A-B-CD-E-F.

The segments A, B, CD, E and F are previously described. The kit also includes RNA ligase, AML reverse transcriptase, Q-beta replicase, a ribozyme that corresponds to the sequences in the CD region, primer for the reverse transcriptase, and buffers, salt and reagent solutions necessary to perform the experiments according to the designed protocol.

It is possible to expect that some detector molecules will be ligated and will fbrm template molecules without annealing with the analyte molecule. Elimination of the background created by these 'accidental' templates will be accomplished by enzymatic degradation and will be performed prior to their amplification with Q-beta replicase. A similar approach was used previously for differentiation of high and low afinity RNA recombinant molecules. After purifying the annealed detector molecule-target analyte complex from the DNA and RNA fragments, non-annealed target analytes and detector molecules, the intact template for Q-beta replicase, protected by the target analyte, will be separated from the target analyte. Amplifying the restored template with Q-beta replicase will indicate the presence of even a small number of target analyte molecules in a specimen.

In a modification of this method to produce two detector-molecules, the recombinant DNA molecules are transribed into RNA before the replication by Q-beta replicase. A RNA polymerase promoter is attached to the nonreplicable portion of the ligated detector-molecules before the transcription.

The attachment of the promoter and transcription of recombinant RNA are used under the standard conditions known to someone skilled in the field of molecular biology.

EXAMPLE 1.

Using the above-cited specifics in the RNA ligase action, we performed an experiment in which the detector probes with captomers formed a 'loose' ternary complex with a nucleic acid target and thus modeled a complex formed by the detector-probes with it protein target. We also investigated the ability of T4 RNA ligase to use such a model complex as a substrate and to restore a template for Q-beta replicase by joining specially-designed captomers.
Preparation of the detector probes.

```
         1        10        20        30        40        50
5'-CGCGTTCGTCCTCACTCTCTTCCGCATCGCTGTCTGCGAGGGCCAGGGCC-3'
   I<-------------------->I I<-------------------->I
         Oligo #3 and #4         Oligo #1 and #2
```

The fifty-base oligonucleotide sequence, SEQ ID NO 1, containing an Hha I- Pvu II region of the late promoter of adenovirus within map units 16.4 and 16.6 (Ziff and Evans, 1978) was chosen as the model target in our experiments. It was synthesized on a DNA Synthesizer, together with two pairs of oligonucleotides—oligos #1 and #2 and oligos #3 and #4.

The first pair of oligos, SEQ ID NO 2 and 3, complement each other and represent the counterparts of the adenovirus target region from the nucleotide $C^{25}$ to the end of the sequence.

```
           XhoI      10        20        30   37
Oligo #1 5'-TCGAGGCCCTGGCCCTCGCAGACAGCGATGAGCTCCC-3'

Oligo #2 3'-CCGGGACCGGGAGCGTCTGTCGCTACTCGAGGG-5'
            33 30        20        10 SacI Sma I
                                       (SstI)
```

Both oligos have additional sequences representing the complete site for Sac I and a half for Sma I restriction enzymes, and the oligo #1 additionally has a sequence of the Xho I restriction enzyme.

Oligos #3 and #4, SEQ ID NO 4 and 5, represent the other half of the adenovirus target molecule and span from the beginning of the target sequence to the $T^{21}$ base.

```
            PpuM-I   10          2022
Oligo #3  5'-AAGAGAGTGAGGACGAACGCGC-3'

Oligo #4  3'-TTCTCTCACTCCTGCTTGCGCGAGCT-5'
             26      20        10   Xho I
```

Both oligos #3 and #4 have half of the recognition site for the PpuM-I restriction site and oligo #4 has a sequence of Xho I restriction enzyme, similar to oligo #1. These two pairs of oligos were also annealed and were used for cloning. They are referred to as the 'PX fragment'. These two pairs of oligos formed two dsDNA fragments, referred to as the 'PX fragment' and 'XS fragment'. They were used for cloning in the recombinant plasmid pT7 MDV-XhoI.

Turning now to FIG. 1, which depicts plasmid pT7 MDV-XhoI, this plasmid was used for cloning of the synthesized PX and XS dsDNAs and for the trascription of the PX and XS recombinant RNA molecules that served as detector molecules for the adenovirus sequences. This plasmid is a variant of the parent plasmid, pT7 MDV, in which the XhoI linker sequence is not present. For further details of the construction of the vector, see Axelrod et al., 1991

The pT7MDV-Xho I plasmid DNA was digested either with Ppu MI and Xho I or with Sma I and Xho I restriction enzymes and purified from the excised 65 bp or 166 bp fragments of the cloned MDV cDNA insert. The remaining parts of the pT7MDV-XhoI plasnid after Ppu MI and Xho I digestion (pT7 MDV-1) contained the T7 promoter and 168 bp 3' end of the MDV cDNA. The remaining part of the pT7MDV-Xho I plasmid digested with Xho I and Sma I enzymes (pT7 MDV-2) contained T7 promoter and the 62 bp 5' end of the MDV cDNA. The PX fragment was ligated with the pT7 MDV-1 and the XS fragment was ligated with pT7 MDV-2, forming pPX and pXS recombinant plasmids. The presence of the two different cloning sites in the digested vector ensures only one possible orientation of the inserts in both the pPX and pXS plasmids. Each of these plasmids contains a T7RNA promoter, an insert homologous to part of the tcrget adenovirus sequence, and a segment of the MDV cDNA.

A control recombinant plasmid with target adenovirus DNA inserts was constructed as well. For this purpose, we modified the original adenovirus sequence so that it contained Xho I sites at both ends similarly to PX and XS fragments. The fragment was then inserted at the Xho I site of pT7 MDV- Xho I, creating plasmid p325. This plasmid was used either to produce the DNA target sequences or to synthesize the recombinant template MDV RNA with an insert of the adenovirus sequences.

Cold or $^{32}$P-labeled RNA was transcribed from plasmids using T7RNA promoter after the Sma I digestion of pPX or p325 and Sst I or Sma I of pXS digestion according to the standard protocols (Sambrook et al., 1989) p The 193-base RNA transcript from the pPX plasmid , SEQ ID NO 6, is composed of (reading in the 5'→3' direction) the first three G residues of transcription initiation, 22 residues transcribed from the PX fragment and 168 residues transcribed from the 3' end of the MI)V cDNA.
5'-GGG-AAGAGAGUGAGGACGAACGCGC-3' MDV-1 RNA (168 bases).

The RNA transcript from the pXS plasmid, SEQ ID NO 7, is only 92 bases, shorter than the pT7MDV-1 transcript, and it starts with the 62 residues of the 5' end MDV cDNA and is followed by the 30 residues transcribed from the XS fragment.
5'-MDV-1 RNA (62 bases)-GGCCCUGGCCCUCGCAGACAGCGAUGAGCU-3'.

An additional three C nucleotides were generated on 3' end of the XS recombinant RNA after Sma I digestion of the same plasmid.

These two recombinant RNAs represent a set of the PX and XS detector molecules. Each of these molecules has three functional parts: amplification, recognition and ligation.
Annealing Experiments PX detector was $^{32}$P end-labeled to monitor the results of the annealing experiments. For this we used bacterial alkaline phosphatase (BAP) and bacteriophage T4 polynucleotide kinase. Both reactions, dephosphorylation and end-labeling, were performed according to standard protocols (Sambrook et al., 1989). Incorporation of the radioactive label was measured in aliquots of the reaction and the percentages of incorporation were calculated.

The PX and SX detector molecules were hybridized with the target adenovirus oligonucleotide sequences. For this the three components were mixed in equal molarity proportion in a range of 2–3 pmole per reaction.

The hybridization produces several radioactive bands, representing the products of association between the target adenovirus DNA and the PX and XS probes.

The annealing reaction products between the PX and XS detector-molecules and adenovirus target sequences were characterized. The annealing reaction was performed with PX and XS RNAs but without adenovirus target molecules. Three separate annealing reactions with PX, XS and adenovirus target molecules were performed. PX recombinant RNA was $^{32}$P end-labeled using standard methods. Annealing was achieved by boiling the reaction mix two minutes and then incubating it at 65° C. for two hours. The annealing reaction was carried out in a solution containing 50 mM TRIS pH 7.8, 5 mM MgCl$_2$, 0.5 mM ATP and 1 mM EDTA, 10% non-denaturing PAGE at 500 volts for eight hours.

The most plausable explanation of the results is that the top band results from the annealing of the target DNA molecule with both RNAs. Such complex is composed of from 50 bp double stranded heteroduplex of target/probes segment and 168 bases 3'-end and 62 bases 5'-end of MDV-I. The lowest band is 193 nucleotides of non-hybridized PX RNA and one of the middle bands, with a size of 243 bases, is a complex between PX RNA and adenovirus DNA molecules. The origin of the second band of similar size is unknown.

The efficiency of hybridization was calculated as a percentage of the radioactivity of the top band from the total radioactivity applied on the gel. Usually more than 50% of the total number of PX RNA molecules participate in hybridization with the adenovirus target molecule by itself or in compound with XS. The yield of the ternary complex formed by two RNA detector molecules and the target molecules was, usually, close to 30–40%.

The diagram below illustrates a possible hybridization configuration between the target adenovirus sequence, SEQ ID NO 1, and the two RNA transcripts. The SX RNA, SEQ ID NO 8, detector, in this case, was generated by Sst I digestion of the pSX plasmid.

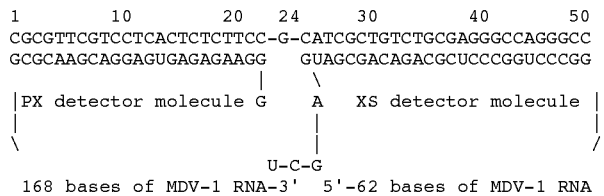

There is complete complementarity along the PX RNA detector and the first 23 bases of the target molecule, but not the last, the 24th G-residue of the transcript and the G-base of the adenovirus target molecule. The first four bases of the XS detector (UCGA) do not have homologous nucleotides on the target DNA molecule, although the rest of the transcript is complementary to the target molecule. Thus, the hybridized RNA transcripts do not juxtapose to the target end-to-end fashion, but rather leave a ~20 Angstrom gap between the terminal hybridized nucleotides.

The G and UCGA nucleotides of the PX and XS detector probes are the captomers. They do not hybridize to the target and comprise structures similar to the donor/acceptor complex, which is necessary in order for RNA ligase to form a phosphodiester bond (Uhlenbeck, 1983). The G captomer is a donor with a 5'-phosphate terminus and the UCGA captomer is an acceptor with a 3'-hydroxyl terminal group on the U residue.

Ligation Experiments

The recombinant plasmid pXS was constructed in a such way that it could be linearized either with SmaI or SstI for RNA transcription (See diagram above). The two XS RNA detector molecules are different in the total lengths and composition of their captomers. The XS detector generated with Sst I digestion had a captomer of four UCGA-base-long base, whereas the captomer generated after the Sma I digestion was longer for the three Cs.

Ligation reactions were carried out on 4 ul aliquots taken directly from the annealing reactions in the presence of the 10 nM mercaptoethanol, and 40 Units of T4 RNA ligase at 25° C. after confirmation by gel electrophoresis that hybridization was successful. The duration of the reaction varied from 2 hours to overnight. The bands representing ligation product composed of PX-SX ligated detector molecules were excited and their radioactivity was measured and compared with the total radioactivity of the aliquot from the annealing reaction used for the ligation.

Products of the ligation reaction and non-ligated PX transcripts were seen on the autoradiographs. The products of the annealing reactions, which were performed with PX and XS transcripts only without the target adenovirus DNAs, served as a negative control. Only PX transcripts were seen compared to Control p325 RNA transcripts. The total volume of each ligation reaction was 10 ul, with the final concentration, 10 mM, 5 mM MgCl$_2$ and 2 Units of T4 RNA ligase in the presence of 20% PEG. The reaction was performed at 25° C. and ended by adding 1 ul of 100 mM EDTA, 7M Urea denatured 10% PAGE at 500 volts for eight hours of electrophoresis.

Additionally, the duration of the reaction apparently does not affect the rate of ligation when the long captomers were used. The yield of the ligated product was 20.0% after two hours of reaction and 18.7% after overnight. The longer reaction time, however, might have a certain disadvantage when the short captomers are used. The overnight reaction yielded 18.4% compared with 33.2% after two hours of reaction. The reduction in the percentages of ligated products after a prolonged reaction time apparently indicate that the ligation products composed of PX and XS RNA transcripts are not stable and dissociate over time. The results of the ligation experiment demonstrates that the length of the XS captomer seemingly does not effect the ligation rate of the RNA transcripts, although the highest ligation rate was observed when the acceptor-captomer was composed of the seven-AGCUCCC-residues. $^{32}$ P-labeled recombinant MDV-I RNA, with the adenovirus insert transcribed from the p325 plasmid, served as a reference marker.

TABLE 1

Effect of the captomer's length on the yield of the ligation products between PX and XS RNA transcripts. 4 ul aliquots of the annealing reactions (1–6*) with two RNA transcripts and adenovirus target DNA were used for the subsequent ligation reaction. 4 ul aliquots of the annealing reaction (7**) without the target DNA were used as the negative control.

| Test # | Length of captomer used in the reaction | Duration of reaction at 25° C. | Total counts (cpm) of the band in the gel | Their proportion (%) from the counts loaded |
|---|---|---|---|---|
| 1. | Short[1] | 2 hours | 3428 | 20.0% |
| 2. | Short | o/n | 3140 | 18.7% |
| 3. | Long[2] | 2 hours | 5576 | 33.2% |

TABLE 1-continued

Effect of the captomer's length on the yield of the ligation products between PX and XS RNA transcripts. 4 ul aliquots of the annealing reactions (1–6*) with two RNA transcripts and adenovirus target DNA were used for the subsequent ligation reaction. 4 ul aliquots of the annealing reaction (7**) without the target DNA were used as the negative control.

| Test # | Length of capto-mer used in the reaction | Duration of reaction at 25° C. | Total counts (cpm) of the band in the gel | Their proportion (%) from the counts loaded |
|---|---|---|---|---|
| 4. | Long | 2 hours | 1657 | 9.9% |
| 5. | Long | o/n | 3085 | 18.4% |
| 6. | Long | o/n | 1385 | 8.2% |
| 7. | Long | 2 hours | 98 | 0.01% |

*--16.800 cpm were loaded into each test lane
**--76.700 cpm were loaded into a control lane The short (UCGA) captomer was generated by the pXS plasmid DNA digestion by the Sst I restriction enzyme, and the long (AGCUCCC) captomer resulted from the digestion of the pXS plasmid DNA by the Sma I restriction enzyme.

The ligation product composed of the ligated PX and XS RNA detector molecules was purified by gel electrophoresis. The purified product was used as a template for Q-beta replicase.

Amplification of the Ligation Products by Q-beta Replicase

Q-beta replicase reactions were carried out on a volume of 20 ul at 37° C. during 25–30 minutes in 50-ul reactions containing 88 mM Tris-HCL (pH 7.5), 12 mM $MgCl_2$, 0.2 mM of each ribonucleoside triphosphate, 25 uCi of [alpha-$^{32}$P]GTP, 90 pm/ml of Q-beta ireplicase, and 11.2 pm/ml of template RNA. From this mixture, 7 to 15 ul was applied directly onto a denaturing polyacrylamide gel containing 7M Urea for electrophoretic analysis. Additionally, adsorbed radioactivity was determined by liquid scintillation.

The Q-beta replicase experiment demonstrates that there are no templates for Q-beta enzyme in the aliquots representing the tube in which the ligation was performed without the adenovirus target, which indicate that target analyte was necessary to unite two detector probes. A ligation reaction was performed on aliquots of the annealing reaction. The 5 ul aliquots from each reaction were analyzed on a non-denaturing gel. An aliquot from the annealing reaction without the adenovirus target sequences, with adenovirus sequence and without PEG, and in the presence of the target adenovirus sequences and PEG (lane 3) were compared to the Q-beta replicase products of pT7 MDV-XhoI plasmid as a control.

The data suggest that amplification of the template by Q-beta replicase occurred only when ligation of the PX and XS RNA detector molecules took place in the presence of the target.

The present invention features a 'flexible' detector-target ternary complex and captomers sections. These features permit use of RNA ligase to restore the ability of recombinant MDV-1 RNA to be a template for Q-beta replicase.

EXAMPLE 2.

A Q-beta replicase-based system of detector-molecules can be constructed and used to identify a protein target in a clinical specimen. As an example we use the high affinity RNA ligand (RRE-aptamer) for Rev protein. The central role of Rev protein in primary and reactivated human immunodeficiency virus type 1 (HIV-1) infections is well studied. The interaction of Rev protein and the cis-acting Rev Responsive Element (RRE) is required for cytoplasmic accumulation of HIV structural proteins encoding viral mRNAs (Malim et al., 1989). Rev protein is essential for infection of HIV-I and without Rev these gene transcripts fail to accumulate, so the virus cannot replicate (Sodroski et al., 1986). The exact mechanism of Rev protein action in HIV infection is still subject to investigation, but it was demonstrated that Rev protein binds the RRE, a segment of a specific structure within mRNA, transporting RREs from host nucleus to cytoplasm (Karn et al., 1991). The Rev protein has been isolated and purified and a series of high affinity aptamers have been selected in various laboratories around the world.

The structure of RRE and the mechanism of interaction between RRE aptamers and Rev protein is well studied. (Karn et al., 1991). The RRE and its aptamers consist of three functional parts. One 'bubble' (the core region), and two double-stranded stems that flank the core region. Experiments with nucleotide substitution showed that the annealing abilities of the whole aptamer depends on the existence of a core region, its nucleotide composition and tertiary configuration. The nucleotide composition of the flanking stems is not crucial as long as the stems ensure the existence of the core region (Giver et al., 1993 a, b ). SELEX-derived oligcnucleotides with $K_d$ are about 10 times lower than those of wild type RRE (Giver et al. ibid). Therefore, RRE aptamers can successfully compete with native RRE for the Rev protein. The Rev protein system and high affinity RNA ligands selected in vitro are used by many research groups as targets for designing an anti-HIV structure-based drug (Klug and Famulok, 1994).

RBE-2, SEQ ID NO 9, a high affinity aptamer selected through SELEX, preserves the structure of the RRE core element, which is supported by two double-stranded stems, and demonstrates high affinity to Rev protein (Bartel et al., 1991). The nucleotides in the core region $U^{45}$→$G^{53}$ and $C^{65}$→$A^{75}$, which are involved in the binding motif for Rev recognition, are shown in italics in the diagram below. A major groove formed in the core region by the two G bases, is underlined and bold in the diagram.

```
                      G
                   G    C G          C
RBE-2 5'-GG U45G  Rev    CAG53CGU    A
      3'-CC A75C         GUC65GCA    A
                   AU   GCA          GU
                      G
```

These two nucleotides open or pull apart the otherwise stringed stem of complementary nucleotides. Such widening is necessary for precise spatial positioning of the Rev peptide's 'epitope' in the major groove. Finally, hydrogen bonds form between the Rev protein and RNA, securing a tight and specific binding into the complex (Iwai et al., 1992).

To construct recombinant RNA molecules containing the aptamer sequences for Rev protein and sequences for the template for Q-beta replicase, the dsDNA representing the whole aptamer with terminal XhoI sites, and the two dsD- NAs representing the halves of the aptamer, are synthesized. These, too, will have appropriate cloning restriction site terminals. The three oligonucleotides are cloned in a pT7 MDV-Xho I plasmid (FIG. 1), using the same strategy and procedures that were performed in model experiments with detector probes specific for the adenc,virus sequences.

```
                             XhoI
Rev protein aptamer  5'--TCGA--GGTGGGCGCAGCGTCAATGACGCTGACGGTACACC--3',          SEQ ID NO 10 and 11
dsDNA                       3'--CCACCCGCGTCGCAGTTACTGCGACTGCCATGTGG--AGCT-5'
                                                                      XhoI XhoI
dsDNAs of first      5'--TCGA--GGTGGGCGCAGCGTCAA--AGCT-3',                        SEQ ID NO 12 and 13
detector molecule           3'--CCACCCGCGTCGCAGTT--TCGA-5'
                                                    SstI PpuMI
dsDNA of second                          5'--AA--TGACGCTGACGGTACACC--3',          SEQ ID NO 14 and 15
detector molecule                        3'--TT--ACTGCGACTGCCATGTGG--AGCT-5'
                                                                       XhoI
```

RNA detector probe transcripts, composed of the RBE-2 and Q-beta replicase template sequences, will be synthesized for each pair of oligos, similar to those of the PX and XS for adenovirus, using the T7 RNA promoter and T7RNA polymerase. The composition of the recombinant RNA transcripts representing the two recombinant RNA detector molecules will be as presented below:

```
5'--62ntMDV--GGUGGGCGCAGCGUCAA--AGCU--3'       SEQ ID NO 16 and 17
5'--GGG--AA--UGACGCUGACGGUACACC--168ntMDV--3',
```

The diagram below (A) demonstrates the possible configuration of the ternary Rev protein-detector probes complex. The detector molecules could be ligated with T4 RNA ligase and will form a single molecule, SEQ ID NO 18, as shown in diagram below (B).

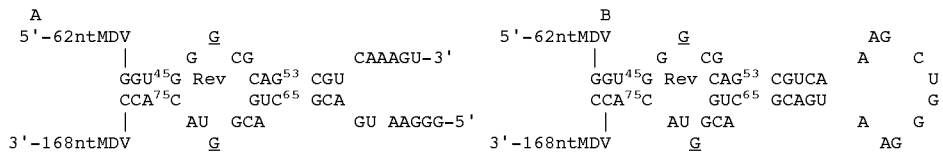

```
 A                                                        B
 5'-62ntMDV      G                                 5'-62ntMDV      G                 AG
          |   G   CG        CAAAGU-3'                       |   G   CG             A     C
         GGU^45G Rev  CAG^53 CGU                           GGU^45G Rev CAG^53 CGUCA       U
         CCA^75C      GUC^65 GCA                           CCA^75C     GUC^65 GCAGU       G
          |   AU  GCA       GU AAGGG-5'                     |    AU GCA            A     G
3'-168ntMDV      G                                3'-168ntMDV      G                  AG
```

The newly constructed aptamer is different from the original by the elongation of the stem between the core region by two base pairs and the loop by five bases, and by the presence of MDV RNA sequences. Its composition is 5'-62ntMDV-RBE-2-168ntMDV-3'.It will be released in a low-salt buffer and MDV reporter templates can be amplified with Q-beta replicase without any additional processing. The number of reporting ligated detector molecules presented in the eluted sample will be proportional to the number of Rev protein molecules in the model samples or clinical specimens, and can be estimated by adding the sample to a standard reaction mixture at 37° C. containing Q-beta replicase and measuring the time required to produce a signal with an intercalating fluorescent dye. Appropriate negative and positive standards will be tested simultaneously with the specimens to establish sensitivity and specificity levels of the assay and to find a correlation between the assay results and the actual HIV titer in the clinical specimens. On the serially diluted Rev protein samples, we will establish a relationship between response time and the number of target molecules in the sample. The response time is universally proportional to the log of the number of template molecules present in the sample (Lomeli et al., 1989). The fluorescence of the amplified detector molecules will be photographed over an ultraviolet light box or measured in a fluorometer. The results of these experiments will enable us to identify the conditions necessary to form the preferred ternary complex of Rev protein and recombinant RNA detector probes with minimal background for the whole assay and, therefore, with high specificity for the whole assay.

Thus, while preferred embodiments have been illustrated and described, it is understood that the present invention is capable of variation and modification and therefore, should not be limited to the precise details set forth, but should include such changes and alterations that fall within the purview of the following claims.

REFERENCES

U.S. PATENT DOCUMENTS

Cech T R., Murphy F L., Zaug A J., Grosshans C., 1992. RNA ribozyme restriction endonucleases and methods. U.S. Pat. No. 5,116,742

Gold L. and C. Tuerk. 1995. Nucleic Acid Ligands. U.S. Pat. No. 5,475,096

Gold L. and S. Rinquist. 1996. Systematic Evolution of Ligands by Exponential Enrichment: Solution SELEX. U.S. Pat. No. 5,567,588.

Hazeloff J P., Gerlach W L., Jennings P A., Cameron F H. 1993. Ribozymes. U.S. Pat. No. 5,254,678.

Martinelli R A., Donahue J J. and Unger T. 1995. Amplification of Midivariant DNA Templates. U.S. Pat. No. 5,407,798

Roberson H D., and Goldberg A R., 1993. Ribozyme Composition and Methods for Use U.S. Pat. No. 5,225,337

OTHER PUBLICATIONS

Axelrod V A., Brown E., Priano C. and Mills D R. 1991. Virology, 184, 595–608

Bartel D P., Zapp M L., Green M R. and J. Szostak. 1991. *Cell* 67,529–536.

Bock et al., 1992, Bock L C., Griffin L C., Lathman J A., Vermaas E H. and Toole J J. 1992. Nature. 355, 564–566.

Dobkin C., Mills D R., Kramer F R. and Spiegelman S. 1979. Biochemistry, 18, 2038–2044.

Engler M J. and Richardson C C. 1982. The enzymes. Academic Press, Inc. vol XV. 3–29.

Ellington A D. and Szostak J W. 1990. *Nature*, 346, 818–822.

Fernandez A., 1991. Z. Naturforsch C. 46, 656–662.

Giver L., Bartel D P., Zapp M L., Green M. and Ellington A D. 1993b. *Gene* 137, 19–24

Gold L., Polisky B., Uhlenbeck O, and Yarus M. 1995. Ann. Rev. Biochem. 64, 763–797.

Iwai S., Pritchard C., Mann D A., Karn J. and Gait M J. 1992. *Nucleic Acid Res.* 20, 6465–6472.

Joyce, G F . 1989. Gene, 82, 83–87.

Karn J., Dingwall C., Finch J T., Heaphy S. and Gait M J. 1991. *Biochimie* 73, 9–16

Kaufmann G., Klein T. and Littauer U Z. 1974. FEBS Lett. 46, 271–275.

Klug S J. and Famulok M. 1994. Mol. Biol. Rep., 20, 97–107

Kubik M F., Stephens A W., Schneider D., Marlar R A. and Tasset D. 1994. Nucleic Acid Res., 22, 2619–2626.

Leis J., Silber R., Malathi V G. and Hurwitz J. 1972. "Advances in the B–iosciences" (G. Raspe, ed) Pergamon, New York. vol. VIII, 117

Lizardi P M., Guerra C E., Lomeli H., Tussie-Luna 1. and Kramer F R. 1988. Biotechnology, 6, 1197–1202.

Lomeli H., Tyagi S., Pritchard C G., Lizardi P. And Kramer F R. 1989. *Clin. Chem.* 35, 1826–1831.

Malim M H., Hauber J, Le S Y Maizel J V and Cullen B R. 1989. *Nature* 338, 254–257.

Meselson M. and Yuang R. 1968. Nature, 217, 1110–1114

Mullis K B, Faloona F, Schraft, Saiki R K, Horn G and Erlich H A. 1986. CSH Symp. Quant Biol., 51, 263–273

Munishkin A V., Voronin L A., Ugarov V I., Bondareva L A., Chetverina H V. and Chetverin A B. 1991. J. Mol. Biol. 221, 463–472.

Nakamura R M. 1993. College of American Pathologists Conference XXIV on Molecular Pathology: Introduction. Ach. Path. Lab. Med., 117, 445–492

Pieken W A., Olsen D B., Bensler F., Aurup H. and Eckstein F. 1991. Science. 253, 314–317.

Priano C., Kramer F R and Mills D R. 1987. Cold Spring Harbor Symp. Quant. Biol. 52, 321–330.

Pritchard C G. and Stefano J E. 1990 Ann. Biol. Clin. 48, 492–497.

Qi An, Buxton D, Hendricks A, Robinson L, Shah J, Ling Lu, Vera-Garcia V, King V and Olive M D. 1995. J. Clin. Microbiol., 33, 860–867

Rys P N and Persing D H. 1993. J Clin Microbiol., 31, 2356–2360.

Saiki R K. 1990. PCR Protocols: a Guide to Methods and Applications. M. A. Innis, D. H. Gelfand. J. J. Sninsky and T. J. White eds. (New York: Academic Press, Inc.), 13–20

Saiki R K, ScharftS, Faloona F et al., 1985. Science., 230, 1350–1354.

Sambrook J., Fritsch E F and T. Maniatis. 1989. Molecular Cloning. Cold Spring Harbor Laboratory Press.

Schneider D J., Feigon J., Hostomsky Z. and Gold L. 1995. Biochemistry 34, 9599–9610.

Silber R. Malathi V G. and Hurwitz J. 1972. Proc. Natl. Acad. Sci. USA 69, 3009–3013

Sodroski J., Goh W C., Rosen C., Dayton A., Terwillinger E and Hasseltine W A. 1986. Nature 321, 412–417

Southern E, 1975. J. Mol. Biol., 98, 503–517.

Sugino A., Goodman H M., Heyneker H L., Shine J., Boyer H M. and Cozzarelli N R. 1977. J. Biol.Chem. 252, 3987–3987

Tyagi S., Landergen U., Tazi M., Lizardi P M. and Kramer F R. 1996. Proc. Natl. Acad. Sci. USA. 93, 5395–5400.

Uhlenbeck O C and Gumport R D. 1982. The enzymes. Academic Press, Inc. vol XV. 31–58.

Uhlenbeck O C. 1983. TIBS. March, 94–96.

Verma I M. 1991. The Enzymes, The Academic Press, vol XIV, 87.

Weissmann C., Feix G. and Slor H. 1968. Cold Spring Harbor Symp. QuLny. Biol. 33, 83–100.

Wu Y., Zhang D Y. and Kramer F R. 1992. Proc. Natl. Acad. Sci. USA. 89, 11769–11773.

Ziff E B. and Evans R M. 1978. Cell 15, 1463–1475.

---

I claim:

1. A first ribonucleic acid (RNA) molecule and a second RNA molecule for use in determining the presence or absence of a target molecule, said first RNA molecule capable of binding to a target molecule and having the following formula:

5'-A-B-C-3';

wherein A is a section of the RNA molecule having 10–100,000 nucleotides which section is capable of being received by an RNA replicase and with another RNA sequence, F, being replicated and the letter "B" denotes a section of the RNA molecule having approximately 10 to 50,000 nucleotides which section is capable of binding to the target molecule and the letter "C" denotes a section of the RNA molecule having approximately 1 to 10,000 nucleotides which section is capable of being ligated to another RNA sequence, "D"; said second RNA molecule capable of binding to said target molecule and having the following formula:

5'-D-E-F-3';

wherein D is a section of the RNA molecule having approximately 1 to 10,000 nucleotides which section is capable being ligated with another RNA sequence, "C", and the letter "E" denotes a section of the RNA molecule having approximately 10 to 100,000 nucleotides which section is capable of binding to the target molecule, and the letter "F" denotes a section of the RNA molecule having 10 to 100,000 nucleotides which section is capable of being received by an RNA replicase and with another sequence, "A", being replicated; said first and the second RNA molecules are capable of forming a third RNA molecule having the following formula:

5'-A-B-C-D-E-F-3';

said third RNA molecule formed by ligating the C and D sections, as the E and the B sections are bound to target, said third RNA molecule capable of being received by an RNA replicase and being replicated by such enzyme as a indication of the presence or absence ol the target molecule.

2. The RNA molecules of claim 1 wherein said sequences represented by the letters "A" and "F" are selected from the group of sequences consisting of MDV-I RNA, Q-beta RNA microvariant RNA, nanovariant RNA, midivariant RNA and modifications of such sequences which maintain the ability of the sequences to be replicated by Q-beta replicase.

3. The RNA molecules of claim 1 wherein the sections B and E bind to the target through non-nucleic acid pairing interactions.

4. The RNA molecules of claim 1 wherein the B and E sections are aptamers or partial aptamers.

5. The RNA molecules of claim 1 wherein the sections C and D together define a site for ligation.

6. A kit for determining the presence or absence of a target molecule comprising a first ribonucleic acid (RNA) molecule and a second RNA, ligase means and amplification means, said first RNA molecule capable of binding to a target molecule and having the following formula:

5'-A-B-C-3';

wherein A is a section of the RNA molecule having 10 to 100,000 nucleotides which section is capable of being received by an RNA replicase and with another RNA sequence, F, being replicated and the letter "B" denotes a section of the RNA molecule having approximately 10 to 50,000 nucleotides, which section is capable of binding to the target molecule, and the letter "C" denotes a section of the RNA molecule having approximately 1 to 10,000 nucleotides, which section is capable of being ligated to another RNA sequence, "D"; said second RNA molecule capable of binding to said target molecule and having the following formula:

5'-D-E-F-3';

wherein D is a section of the RNA molecule having approximately 1 to 10,000 nucleotides which section is capable being ligated to another RNA sequence, "C", and the letter "E" denotes a section of the RNA molecule having approximately 10 to 50,000 nucleotides which section is capable of binding to the target molecule, and the letter "F" denotes a section of the RNA molecule having 10 to 100,000 nucleotides which section is capable of being received by an RNA replicase and with another sequence, "A", being replicated; said first and the second RNA molecules are capable of forming a third RNA molecule having the following formula:

5'-A-B-C-D-E-F-3';

said third RNA molecule formed by ligating the C and D sections, as the E and the B sections are bound to target, said third RNA molecule capable of being received by an RNA replicase and being replicated by such enzyme as a indication of the presence or absence of the target molecule; said ligase means capable of forming said third RNA molecule in the presence of said complex and said amplification means capable of forming a plurality of said third RNA molecule or a corresponding RNA or DNA molecule in the presence of said third molecule.

7. A method of making a first ribonucleic acid (RNA) molecule and a second RNA molecule for use in determining the presence or absence of a target molecule, said first RNA molecule capable of binding to a target molecule and having the following formula:

5'-A-B-C-3';

wherein A is a section of the RNA molecule having 10–100,000 nucleotides which section is capable of being received by an RNA replicase and with another RNA sequence, F, being replicated and the letter "B" denotes a section of the RNA molecule having approximately 10 to 50,000 nucleotides which section is capable of binding to the target molecule and the letter "C" denotes a section of the RNA molecule having approximately 1 to 10,000 nucleotides which section is capable of being ligated to another RNA sequence, "D"; said second RNA molecule capable of binding to said target molecule and having the following formula:

5'-D-E-F-3';

wherein D is a section of the RNA molecule having approximately 1 to 10,000 nucleotides which section is capable being ligated with another RNA sequence, "C", and the letter "E" denotes a section of the RNA molecule having approximately 10 to 100,000 nucleotides which section is capable of binding to the target molecule, and the letter "F" denotes a section of the RNA molecule having 10 to 100,000 nucleotides which section is capable of being received by an RNA replicase and with another sequence, "A", being replicated, said first and the second RNA molecules are capable of forming a third RNA molecule having the following formula:

5'-A-B-C-D-E-F-3';

said third RNA molecule formed by ligating the C and D sections, as the E and the B sections are bound to target, said third RNA molecule capable of being received by an RNA replicase and being replicated by such enzyme as a indication of the presence or absence of the target molecule; comprising the step of combining a sample containing the target molecule with a library of RNA molecules having the formula:

5'-A-B'-C-D-E'-F-3';

to form a mixture of one or more target bound RNA molecules and one or more unbound RNA molecules, wherein the letters B' and E' are sections with randomized nucleotides and represent potential sections B and E; combining primer nucleic acid corresponding to at least one section with the mixture with an enzyme capable of degrading the unbound RNA molecules and imposing conditions for degradation; releasing said bound RNA molecules from target; and amplifying said bound RNA molecules with an RNA replicase to form an amplification product having the formula:

5'-A-B'-C-D-E'-F-3';

cleaving said amplification product to form the first and second RNA molecules.

8. The method of claim 7 wherein said sections B' and E' are randomized nucleotide sequences.

9. A kit for performing the method of claim 7 comprising one or more sections of the third RNA molecule and an amplification enzyme.

10. A first ribonucleic acid (RNA) molecule and a second RNA molecule for use in determining the presence or absence of a target molecule, said first RNA molecule capable of binding to a target molecule and having the following formula:

5'-A-B-C-3';

wherein A is a section of the RNA molecule having 10–100,000 nucleotides which section is capable of being received by an RNA replicase and with another RNA sequence, F, being replicated and the letter "B" denotes a section of the RNA molecule having approximately 10 to 50,000 nucleotides which section is capable of binding to the target molecule through non-Watson-Crick binding and the letter "C" denotes a section of the RNA molecule having approximately 1 to 10,000 nucleotides which section is capable of being ligated to another RNA sequence, "D", with an RNA ligase; said second RNA molecule capable of binding to said target molecule and having the following formula:

5'-D-E-F-3';

wherein D is a section of the RNA molecule having approximately 1 to 10,000 nucleotides which section is capable being ligated with another RNA sequence, "C" with an RNA ligase, and the letter "E" denotes a section of the RNA molecule having approximately 10 to 100,000 nucleotides which section is capable of binding to the target molecule through non-Watson-Crick binding, and the letter "F" denotes a section of the RNA molecule having 10 to 100,000 nucleotides which section is capable of being received by an RNA replicase and with another sequence, "A", being replicated; said first and the second RNA molecules are capable of forming a third RNA molecule having the following formula:

5'-A-B-C-D-E-F-3';

said third RNA molecule formed by ligating the C and D sections, as the E and the B sections are bound to target, said third RNA molecule capable of being received by an RNA replicase and being replicated by such enzyme as a indication of the presence or absence of the target molecule.

* * * * *